(12) United States Patent
Bugedo-Albizuri et al.

(10) Patent No.: US 11,992,390 B2
(45) Date of Patent: May 28, 2024

(54) RIBBON WOUND DRESSING

(71) Applicant: Advanced Medical Solutions Limited, Winsford (GB)

(72) Inventors: Ander Bugedo-Albizuri, Winsford (GB); Brian John Hamerslagh, Higher Runcorn (GB); Colin Raymond Bradford, Keighley (GB)

(73) Assignee: Advanced Medical Solutions Limited, Cheshire (GB)

( * ) Notice: Subject to any disclaimer, the term of this patent is extended or adjusted under 35 U.S.C. 154(b) by 78 days.

(21) Appl. No.: 16/711,906

(22) Filed: Dec. 12, 2019

(65) Prior Publication Data
US 2020/0188179 A1    Jun. 18, 2020

(30) Foreign Application Priority Data
Dec. 13, 2018    (GB) ..................... 1820336

(51) Int. Cl.
*A61F 13/01* (2024.01)
*A61F 13/00* (2024.01)

(52) U.S. Cl.
CPC .. *A61F 13/01042* (2024.01); *A61F 13/01017* (2024.01); *A61F 13/01029* (2024.01); *A61F 2013/00148* (2013.01); *A61F 2013/0054* (2013.01); *A61F 2013/0074* (2013.01)

(58) Field of Classification Search
CPC ................ A61F 13/00; A61F 13/00004; A61F 13/00008; A61F 13/00021; A61F 13/00029; A61F 13/00034; A61F 13/00042; A61F 13/00017; A61F 13/069; A61F 2013/00148; A61F 2013/0054; A61F 2013/0074; A61F 2013/00089; A61F 2013/00102; A61F 2013/00544; A61F 2013/00604; A61F 2013/00361; A61F 2013/00634; A61F 5/01; A61F 2/0009; A61F 2013/00217; A61F 13/01; A61F 13/01021; A61L 31/146
USPC ...... 602/41–43, 46, 60–66, 75; 128/887–894
See application file for complete search history.

(56) References Cited

U.S. PATENT DOCUMENTS

| 1,630,855 | A | * | 5/1927 | Mahnk ..................... G09F 3/00 40/1.5 |
| 5,795,921 | A | | 8/1998 | Dyer et al. |
| 2005/0148920 | A1 | | 7/2005 | Addison |
| 2008/0132820 | A1 | | 6/2008 | Buckman et al. |
| 2018/0133067 | A1 | * | 5/2018 | Ikai ..................... A61F 13/0243 |

FOREIGN PATENT DOCUMENTS

| CA | 3044955 A1 | 7/2018 |
| CN | 107286313 A * | 10/2017 |
| GB | 2509160 A | 6/2014 |

(Continued)

OTHER PUBLICATIONS

Machine translation of CN 107286313 A (Year: 2017).*
(Continued)

*Primary Examiner* — Caitlin A Carreiro
(74) *Attorney, Agent, or Firm* — Michael Best & Friedrich LLP

(57) ABSTRACT

An elongate wound dressing for packing a wound is substantially planar and has a first longitudinal edge comprising at least one curved edge portion which is curved in the plane of the wound dressing.

15 Claims, 9 Drawing Sheets

(56) References Cited

FOREIGN PATENT DOCUMENTS

| WO | 92/05756 A1 | 4/1992 | | |
|---|---|---|---|---|
| WO | WO-9205756 A | * | 4/1992 | ........... A61F 13/069 |
| WO | WO-9205756 A1 | * | 4/1992 | |
| WO | 2014/013348 A2 | | 1/2014 | |
| WO | 2015/000610 A1 | | 1/2015 | |
| WO | WO-2017212292 A1 | * | 12/2017 | ............. A61F 13/00 |
| WO | 2018/044944 A1 | | 3/2018 | |
| WO | 2018/217621 A1 | | 11/2018 | |
| WO | 2019/003183 A1 | | 1/2019 | |

OTHER PUBLICATIONS

Great Britain Patent Office Search Report for Application No. GB1820336.4 dated May 23, 2019 (4 pages).
European Patent Office Extended Search Report for Application No. 19215928.3 dated Apr. 20, 2020 (8 pages).
Anonymous: "Gazin Ribbon Gauze I Medical Supplies", May 9, 2023 (May 9, 2023), XPO93O45314, Retrieved from the Internet: URL:https://www.praxisdienst.com/en/Dressing+Material/Bandage+Material/Ribbon+Gauze/Gazin+Ribbon+Gauze+1+PC+1+cm.html [retrieved on May 9, 2023].
Lohmann & Rauscher: "Gazin Ribbon Gauze, sterile", Mar. 1, 2012 (Mar. 1, 2012), XPO93O45316, Retrieved from the Internet: URL:https://www.vho.be/media/assets/b3d2867cee6a-11e9-8a64-005056983846/GAZINWIEKtechnischefiche.pdf [retrieved on May 9, 2023].
European Patent Office Action for Application No. 19215928.3 dated May 15, 2023 (6 pages).

* cited by examiner

RIBBON WOUND DRESSING

CROSS-REFERENCE TO RELATED APPLICATION

This patent application claims priority to United Kingdom Patent Application No. 1820336.4, filed Dec. 13, 2018, the entire content of which is hereby incorporated by reference.

BACKGROUND

Physical trauma to the skin of a mammalian body may result in wounds which may require prolonged periods of time to heal. Such wounds may be inflicted by surgical or non-surgical means, and may be generally classified into deep wounds, cavity wounds and tunnelling wounds. Tunnelling wounds are particularly difficult to treat as they may extend beyond the subcutaneous tissue, and in extreme circumstances, may even extend into muscle tissue. Further challenges in the treatment of tunnelling wounds reside in their variable shape, length and directionality through the subcutaneous tissue. The difficulties in the treatment of wounds may further be exacerbated by infection, which can cause inflammation and hinder the healing process.

Treatment methods of deep wounds include secondary intention where the wound is left open and allowed to close up naturally. Healing of the wound tends to occur from the base of the wound up towards the surface (i.e. the skin), and as such the depth of the wound decreases with time until it is completely healed. When treating wounds by means of secondary intention, it is often necessary to pack the wound with a medical dressing to absorb exudate and to mitigate the risk of infection.

Medical dressings used for packing wounds are typically elongated to facilitate the application of the dressing to the base of the wound, which may be deep within the tissue. The elongated medical dressings are typically of a diameter which enables access to the wound. Furthermore, elongation of the dressing allows the dressing to be folded in on itself within the wound, to provide a packing. Elongate medical dressings may also be referred to as ribbon dressings. They differ from other types of dressing in that they are inserted into a wound as opposed to being rested on top of it.

During the course of healing, the medical dressing typically requires changing for a fresh dressing several times in order to prevent infection, to allow repacking of the wound to accommodate for newly formed tissue (also known as granulation tissue), and to remove dressings which are saturated with exudate. Furthermore, regular changing of the medical dressings allows inspection of the healing process, and thus mitigates the risk of serious infection going unnoticed or irregular healing occurring. As such, it is important to ensure that removal of medical dressings does not damage the delicate granulation tissue which in turn may cause the wound to open up further. It is therefore desirable that medical wound dressings can be easily applied and removed without causing undue pain to the patient, or damage to their wound.

Ribbon wound dressings which are typically of rectangular shape. They may be provided in rolls of variable width and length, and cut to an appropriate size for use in treatment. Cylindrically shaped ribbon wound dressings, which may also be known as rope dressings, are difficult to effectively fold and pack into a wound due to their shape. As such, rectangular shaped ribbon wound dressings are preferred as the flat upper and lower surfaces provide a more effective means for folding the wound dressing in use.

However, where a rectangular ribbon wound dressing is applied to a wound and folded therein, the folded ribbon dressing results in sharp corners and edges being formed at each folding juncture. FIG. 1A shows an illustrative plan view of a ribbon wound dressing, with the points of folding represented by dashed lines. FIG. 1B shows an illustrative ribbon wound dressing that has been folded, and some of the resulting sharp corners and edges are indicated by arrows. The corners of the folded ribbon dressing may abut against the inside of the deep wound, causing pain to the patient. This is a particular issue where the medical dressing is made of an absorbent material which expands on absorption of wound exudate. As the dressing absorbs exudate from the wound in situ, the dressing expands forcing the sharp corners of the dressing into the walls of the wound. The expansion of the wound dressing may therefore cause discomfort to the patient. In addition, the sharp corners abutting the walls of the wound may prevent efficient healing thereof.

Furthermore, when folded in a wound as packing, ribbon and rope wound dressings may adhere to the inner surface of the wound cavity. This can cause pain to the patient when the dressing is removed, particularly if the wound dressing has become dehydrated following a prolonged period of residence in the wound. It may be desirable in such circumstance to re-wet the wound dressing prior to removal to reduce the adherence, however detachment and disruption of newly formed issue is a common occurrence. Removal of dressings under these circumstances thus causes disruption of the healing wound, and increases the time it takes for the wound to effectively heal.

Folding a ribbon wound dressing within a wound may also result in areas of the wound not being effectively packed, thus leaving regions of the wound at risk of harbouring infections and prolonging the healing process. This is because the rectangular ribbon wound dressing when folded comprises a series of stacked quadrilaterals which do not afford an accurate representation of (or conform accurately to) wound profiles.

Existing ribbon wound dressings are typically made of hydrophilic materials such as non-woven hydrophilic fibres. Non-woven hydrophilic fibres typically comprise materials such as alginate, sodium Carboxymethyl cellulose, Ethyl sulfonate, cellulose fibres, polyvinyl alcohol fibres, chitosan gelling fibres, other fibres and combinations thereof. However, such materials often leave residual fibres in the wound when removed which may cause the wound to become infected if they are not adequately removed. Such materials may lose their structural integrity following absorption of exudate from the wound, in part, due to the fibre gelling process. Therefore, when the dressing is removed from the wound, the dressing may break up, or even disintegrate entirely, leaving fibres of the dressing in the wound, or even significant parts of the dressing. Unless the wound dressing is bioresorbable, the residual dressing portions will require removal to avoid healing complications. For example, residual fibres in the wound may lead to the formation of a foreign body granuloma, which is likely to have a negative impact on the wound healing response, and in addition may constitute the need for surgical intervention. This problem has in part been addressed by reinforcing the material from which the dressing is made, for example by providing threads throughout the structure [see WO2009136160 (A1)], but has not alleviated the issue in full as residual dressing fibres still remain. The continued structural integrity of the wound dressing both when dry and when wet with exudates after use is therefore an ongoing challenge. Furthermore, such hydrophilic materials are also known to expand significantly within the wound causing significant and undesirable pressure on the walls of the healing wound. It is therefore common practice to loosely pack a wound dressing in a wound to avoid undesirable pressure exerted by the exudate-absorbed dressing on the wound wall.

It is an object of the present invention to address one or more of the above-mentioned problems.

SUMMARY OF INVENTION

The present invention relates to elongate wound dressings for packing a wound. The skilled person will understand that wounds that may be packed are wounds which penetrate the surface of the skin. In some circumstances, the wound penetrates through the subcutaneous tissue, and in severe circumstances may also penetrate into muscle tissue. Wounds may include deep wounds, cavity wounds, tunnelling wounds and/or chronic wounds. The skilled person will understand that elongate wound dressings typically have opposing longitudinal edges, and opposing transverse edges wherein the longitudinal edges are longer in length as compared to the transverse edges. The present invention relates to in particular, but not exclusively, ribbon wound dressings.

According to a first aspect of the present invention, there is provided an elongate wound dressing for packing a wound, the wound dressing being substantially planar and having a first longitudinal edge comprising at least one curved edge portion which is curved in said plane of the wound dressing. The curved edge portion being curved in the plane of the elongate wound dressing results in the width (perpendicular to a longitudinal axis of the wound dressing) of the elongate wound dressing being variable along portions of its length that are characterised by a curved edge portion of a longitudinal edge. As such, a plan view perspective of the elongate wound dressings according to the present invention reveals the curved profile of the curved edge portion.

Advantageously, the wound dressing being substantially planar allows the wound dressing to be efficiently folded. The faces of adjacent/opposing fold sections can be substantially overlaid, providing greater packing efficiency as compared to non-planar wound dressings.

The folding of conventional rectangularly-shaped ribbon wound dressing creates two corners at each fold intersection (or fold line or fold axis). Thus the number of corners in a packed (i.e. folded) ribbon wound dressing may be considered to be 2n+4 where n is the number of folds. In conventional ribbon wound dressings, these corners abut the inside of a wound, causing discomfort and pain to the patient, particularly where the dressing has expanded through absorption of exudates.

Advantageously, the at least one curved edge portion being curved in the plane of the wound dressing reduces the number of corners abutting the inside of a wound when the wound dressing is packed into a wound. The curved edge portions of the elongate wound dressing according to the present invention provide a curved surface which abuts the inside of the wound when the elongate wound dressing is packed into it. As curves are typically smooth, the pressure of the wound dressing abutting the walls of a wound is spread over a larger surface area as compared to a corner, and as such pain caused to a patient is reduced. The present invention therefore mitigates the abutment of sharp corners against the inside of a wound.

In addition, the corners created by folding of the wound dressing according to the present invention are advantageously urged away from the walls of the wound by means of the curved edge profile. Furthermore, the corners that are created through folding of the elongate wound dressings according to the present invention are typically at the narrowest points of the ribbon wound dressing, therefore confining the fold corners to a restricted portion of the wound dressing and minimising the corner surface area in contact with the wound. Reducing the contact of corners with the wound mitigates the pain caused to patients by corners of wound dressings abutting the interior walls of the wound, particularly as the wound dressing expands in situ by absorbing exudates.

Furthermore, the curved profile of the curved edge portion may provide a more complimentary shape to the interior of a wound as compared to conventional rectangularly-shaped ribbon wound dressings, thereby enabling improved healing of the wound. Conventional ribbon wound dressings rely on expansion of the ribbon wound dressing in situ to fill gaps and voids in the wound. However, the cuboidal profile of a folded rectangular ribbon wound dressing is a poor representation of the interior shape of a wound, which is typically irregular and comprises curved inner surfaces. The present invention provides a curved profile which may better extend into the extremities of a wound as compared to existing ribbon wound dressings.

In some embodiments, the elongate wound dressing has a second longitudinal edge comprising at least one curved edge portion which is curved in said plane of the wound dressing. Advantageously, both the first and second longitudinal edges of the ribbon wound dressing comprising curved edge portions further minimises the number or corners abutting the wound during use.

In some embodiments, the curved edge portion of the first longitudinal edge has a corresponding profile to the curved edge portion of the second longitudinal edge, such that the first longitudinal edge of the elongate wound dressing tessellates with a second longitudinal edge of an identical elongate wound dressing. Advantageously, tessellation of individual ribbon wound dressings reduces the amount of waste material created during the manufacturing process.

In some embodiments, the elongate wound dressing is symmetrical in a plane that is perpendicular to the plane of the elongate wound dressing, and which bisects the wound dressing along a central longitudinal axis. Advantageously, a symmetrical elongate wound dressing improves the packing efficiency of the wound dressing, and further aids the tessellation of the elongate wound dressings.

In some embodiments, the elongate wound dressing is tapered along at least a portion of its length in the plane of the wound dressing relative to the central longitudinal axis of the elongate wound dressing. Advantageously, tapering of the wound dressing may provide for better packing of wounds which have a narrower base as compared to the wound opening, or conversely for wounds that have a broader base as compared to the wound opening.

In some embodiments, the at least one curved edge portion comprises a plurality of co-planar curved protrusions projecting outwardly relative to the central longitudinal axis of the elongate wound dressing and in the plane of the wound dressing. Advantageously, the co-planar curved protrusions means that the elongate wound dressing is substantially two-dimensional, and thus can be easily folded.

In some embodiments, the elongate wound dressing comprises a central rectangular portion of width W, and the plurality of co-planar curved protrusions project outwardly from the notional longitudinal edge of the central rectangular portion. A notional edge of the rectangular portion may also be referred to a an imaginary, conceptual, theoretical or hypothetical edge—that is to say, it is not an edge that exist in reality, but merely as a concept as part of the wound dressing to aid the reader understanding the shape of the dressing.

In some embodiments each protrusion is convex in shape.

In some embodiments, the plurality of protrusions form an undulating profile along the curved edge portion. Advantageously, the undulating profile means the curved edge portion is entirely devoid of any sharp corners. The undulating profile may be periodic, for example, but not limited to, sinusoidal.

In some embodiments, the curved edge portion extends around the entire perimeter of the elongate wound dressing, that is to say the first longitudinal edge, the second longitudinal edge, and both ends of the wound dressing each have a curved edge portion which form a single continuous curved edge portion around the perimeter of the wound dressing. In other words, the longitudinal edges and ends are all curved.

In some embodiments, the elongate wound dressing comprises a rectangular central portion of width W wherein the elongate wound dressing is foldable along portions of the wound dressing of width W. The elongate wound dressing may be foldable along a fold axis which is perpendicular to the longitudinal axis of the dressing.

In some embodiments the portions of the wound dressing having width W are devoid of protrusions and/or are located between adjacent protrusions. Advantageously, portions of the elongate wound dressing that are devoid of protrusions can form portions suitable as folding junctures.

In some embodiments adjacent protrusions are axially separated with respect to the central longitudinal axis of the wound dressing. Advantageously, separating the protrusions in this way provides sufficient material to form a fold, such that a protrusion may be transposed onto an adjacent protrusion. The skilled person will understand that transpose within this context means that the elongate wound dressing may be folded such that two adjacent protrusions substantially overlap.

In some embodiments each protrusion extends outwardly (to a maximum distance from the longitudinal axis) to increase the maximum width of the elongate wound dressing to between 1.1 times W and 2 times W. In some embodiments each protrusion extends outwardly to increase the maximum width of the elongate wound dressing by around 1.5 times W. Advantageously, these dimensions ensure that the central rectangular portion of the wound dressing provides adequate strength to the elongate wound dressing, and furthermore ensures that the protrusions do not extend so far that they may tear away from the central rectangular portion of the wound dressing.

In some embodiments, the elongate wound dressing comprises an absorbent layer, a first non-adherent layer, and a second non-adherent layer, wherein the absorbent layer is disposed between the first non-adherent layer and the second non-adherent layer. Advantageously, the elongate wound dressing may thus be provided in a laminate type structure. Advantageously, large sheets of laminate may be produced, and the elongate wound dressings cut therefrom. Advantageously, the wound dressings may be cut from the laminate such that the wound dressings tessellate, thereby reducing waste laminate material during the manufacturing process. In addition, the laminate structure advantageously provides enhanced structural integrity to the elongate wound dressing, as compared to non-woven hydrophilic fibres which may degrade back into fibres following absorption of exudate. The laminate structure ensures that the structural integrity of the wound dressings according to the present invention is maintained whether the dressings are dry or wet with exudates. Furthermore, advantageously, the laminate structure improves the conformability and increases the tensile strength of the elongate wound dressings, allowing folds to be easily made without fear of comprising the structural integrity of the fold itself.

In some embodiments, the first non-adherent layer and/or the second non-adherent layer is perforated. The first non-adherent layer and/or the second non-adherent layer may be a breathable polymeric film or a mesh. Advantageously perforations in the non-adherent layers enable the elongate wound dressing to breathe during use, that is to say exudate moisture may be transmitted from the absorbent layer through the dressing to the surface of the wound where it may evaporate. Transmission of moisture in this way through the dressing and away from the wound may prevent infection of the wound, or saturation of the wound dressing with exudates. In some embodiments, the first non-adherent layer and/or the second non-adherent layer may be a polyurethane layer.

In some embodiments the absorbent layer comprises a foam. Advantageously, the porous structure of the foam enables quick absorption of exudates from the wound.

Advantageously, foam layers do not significantly expand on absorption of exudates. As such, the pressure exerted by the wound dressing against the internal walls of the wound during use is reduced compared to conventional ribbon wound dressings which may comprise hydrophilic non-woven fibres. In some embodiments, the absorbent layer may comprise hydrophilic non-woven fibres.

In some embodiments the absorbent layer comprises polyurethane foam. Polyurethane foam has been found to be particularly suitable for application in the present invention, owing to its low expansion during absorption of exudates, and furthermore due to superior structural integrity when wet with exudates, as compared to conventional hydrophilic, non-woven fibres.

According to a second aspect of the present invention, there is provided an elongate wound dressing comprising an absorbent layer, a first non-adherent layer, and a second non-adherent layer, wherein the absorbent layer is disposed between the first non-adherent layer and the second non-adherent layer. Advantageously, the elongate wound dressing may thus be provided in a laminate type structure. Advantageously, large sheets of laminate may be produced, and the elongate wound dressings cut therefrom. Advantageously, the wound dressings may be cut from the laminate such that the wound dressings tessellate, thereby reducing waste laminate material during the manufacturing process. In addition, the laminate structure advantageously provides enhanced structural integrity to the elongate wound dressing, as compared to non-woven hydrophilic fibres which may degrade back into fibres following absorption of exudate. The laminate structure ensures that the structural integrity of the wound dressings according to the present invention is maintained whether the dressings are dry or wet with exudates. Furthermore, advantageously, the laminate structure improves the conformability and increases the tensile strength of the elongate wound dressings, allowing folds to be easily made without fear of comprising the structural integrity of the fold itself.

In some embodiments, the first non-adherent layer and/or the second non-adherent layer is perforated. The first non-adherent layer and/or the second non-adherent layer may be a breathable polymeric film or a mesh. Advantageously perforations in the non-adherent layers enable the elongate wound dressing to breathe during use, that is to say exudate moisture may be transmitted from the absorbent layer through the dressing to the surface of the wound where it may evaporate. Transmission of moisture in this way through the dressing and away from the wound may prevent infection of the wound, or saturation of the wound dressing with exudates. In some embodiments, the first non-adherent layer and/or the second non-adherent layer may be a polyurethane layer.

In some embodiments, the absorbent layer comprises a foam. Advantageously, the porous structure of the foam enables quick absorption of exudates from the wound. Advantageously, foam layers do not significantly expand on absorption of exudates. As such, the pressure exerted by the wound dressing against the internal walls of the wound during use is reduced compared to conventional ribbon wound dressings which may comprise hydrophilic non-woven fibres. In some embodiments, the absorbent layer may comprise hydrophilic non-woven fibres.

In some embodiments the absorbent layer comprises polyurethane foam. Polyurethane foam has been found to be particularly suitable for application in the present invention, owing to its low expansion during absorption of exudates, and furthermore due to superior structural integrity when wet with exudates, as compared to conventional hydrophilic, non-woven fibres.

The elongate wound dressing may have features corresponding with those described in relation to the first aspect of the invention.

According to a third aspect of the present invention, there is provided an elongate wound dressing for packing a wound comprising a polyurethane absorbent layer. The polyurethane absorbent layer may be a polyurethane absorbent foam. The elongate wound dressing for packing a wound may correspond with that described with reference to the first or second aspects of the invention.

LIST OF FIGURES

The present invention will now be described by way of example only, and with reference to the accompanying Figures in which.

DETAILED DESCRIPTION

Figure 1A:
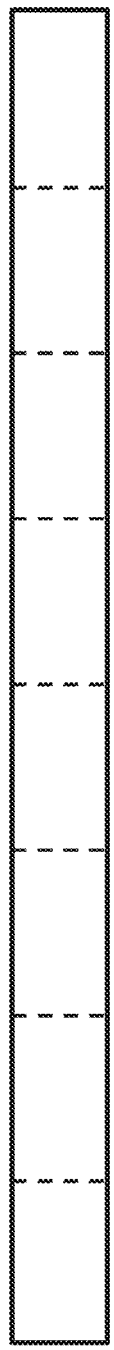
FIG. 1A depicts an illustrative plan view of a conventional ribbon wound dressing.
Figure 1B:
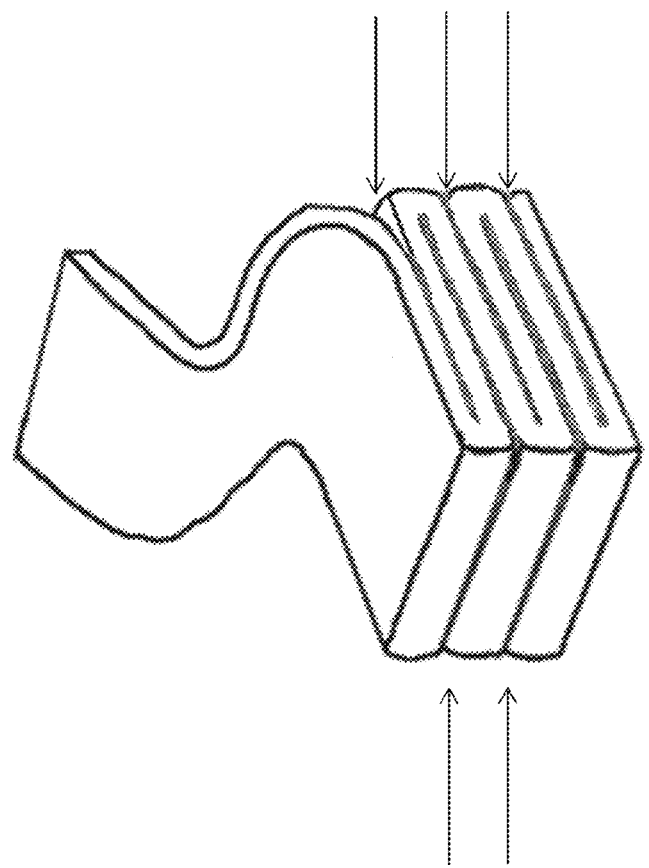
FIG. 1B depicts an illustrative conventional ribbon wound dressing that has been folded.
Figure 2:
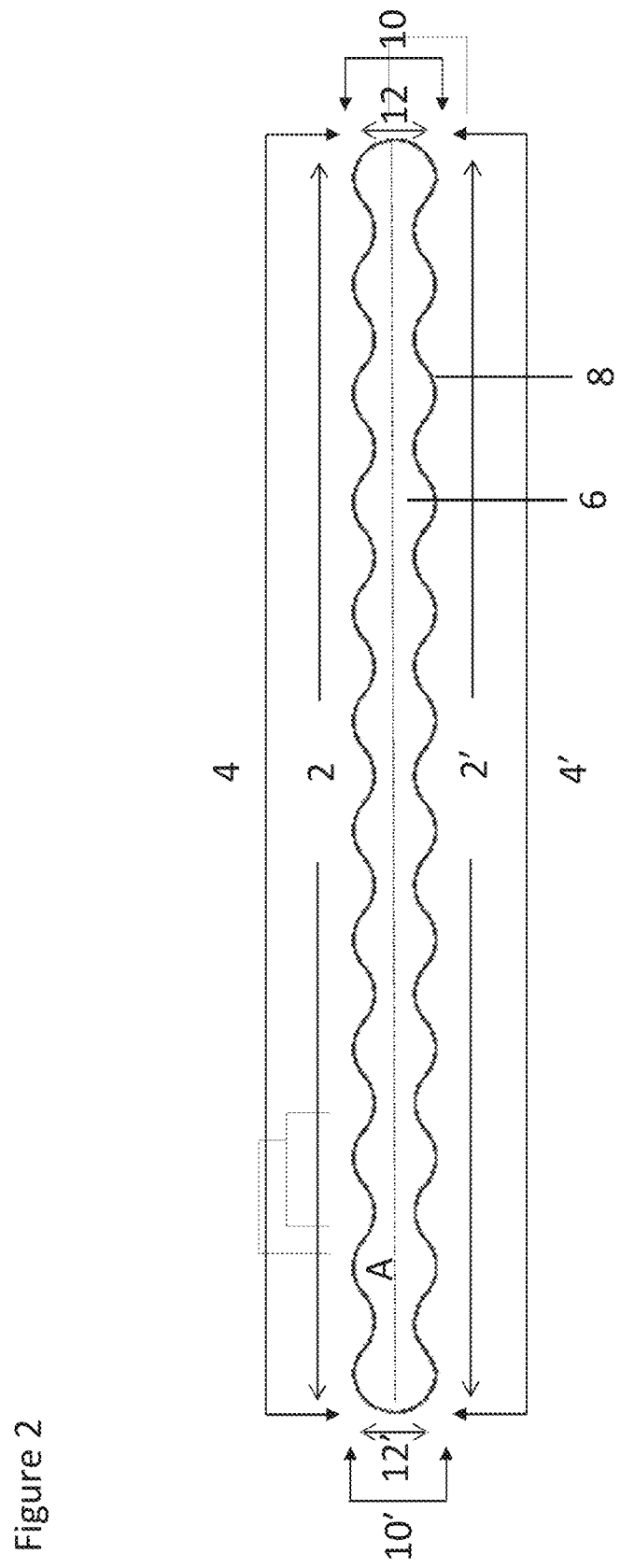
FIG. 2 depicts a plan view of an elongate wound dressing according to the present invention.

The elongate wound dressings according to the present invention are suitable for packing a wound, in particular but not limited to deep wounds, cavity wounds, chronic wounds and tunnelling wounds. FIG. 2 depicts an illustrative embodiment of the present invention in plan view. The dressing comprises a curved edge portion 2 running along the length of the first longitudinal edge 4 and a second curved edge portion 2' running along the length of the second longitudinal edge 4'. The dressing has a central longitudinal axis A which runs through the centre of the dressing. The upper surface 6 of the wound dressing can be seen, and the lower surface 8 is occluded from view in FIG. 2 by the upper surface 6. The upper 6 and lower 8 surfaces are substantially planar and as such are substantially flat along the length of the elongate wound dressing. The upper 6 and lower 8 faces are disposed between (or at least partially bounded by) the first 4 and second 4' longitudinal edges. In some embodiments, the wound dressing comprises a first transverse edge 10 which may comprise a curved edge portion 12. In some embodiments, the wound dressing comprises a second transverse edge 10' comprising a curved edge portion 12'. The first 10 and second 10' transverse edges are each disposed between the first 4 and second 4' longitudinal edges.

Referring to FIG. 2, in some embodiments, the curved edge portion 2 extends along the entire length of the first longitudinal edge 4. In some embodiments, the curved edge portion 2' extends along the entire length of the second longitudinal edge 4'. In some embodiments, both curved edge portions 2, 2' extend along the entire length of the first 14 and second 14' longitudinal edges respectively.

In some embodiments, the elongate wound dressing comprises a continuous curved edge portion about its perimeter, such that the first 4 and second 4' longitudinal edges, and the first 10 and second 10' transverse edges have a single curved edge portion in common (i.e. curved edge portions 2, 2', 12, and 12' form a continuous single curved edge portion). An exemplary embodiment with this arrangement is illustrated in FIG. 2.

In some embodiments, each longitudinal edge comprises more than one curved edge portion. In some embodiments, only a portion of each longitudinal edge 4, 4' comprises a curved edge portion, as depicted in FIGS. 3A-3D.

Figure 3A:
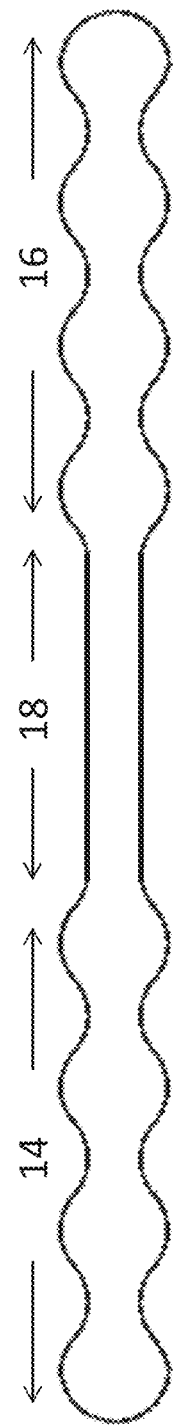
FIGS. 3A-3D depicts different illustrative embodiments of the present invention having different curved edge portions.
Figure 3B:
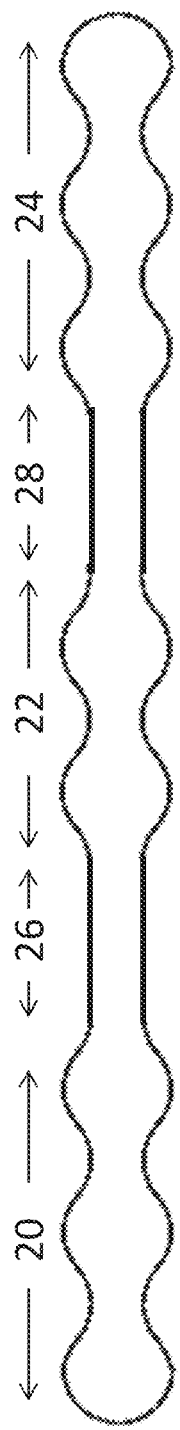
Figure 3C:
Figure 3D:

In FIG. 3A, the first longitudinal edge 4 (and second 4') comprises first curved edge portion 14 and second curved edge portion 16. Portion 18 of the elongate wound dressing is devoid of a curved edge, and so only a portion of the first longitudinal edge comprises a curved edge portion. As depicted in FIG. 3B, the first longitudinal edge 4 (and second 4') comprises a first curved edge portion 20, a second curved edge portion 24 and a third curved edge portion 22. The first 20 and second 22 curved edge portions are separated by portion 26 which is devoid of a curved edge. The second 22 and third 24 curved edge portions are separated by portion 28 which is devoid of a curved edge. In some embodiments, a portion of the elongate wound dressing adjacent the first 10 or second 10' transverse edges is devoid of a curved edge portion. Referring to FIG. 3C, a terminal portion 30 (or terminal end) of the wound dressing, that is a portion extending from the second transverse edge 10', is devoid of a curved edge (and hence a curved edge portion). In other words, at the terminal portion, each of the transverse edge, the first longitudinal edge and the second longitudinal edge are devoid of a curved edge. This arrangement may be useful where a medical practitioner requires a tab for gripping when removing the wound dressing from a wound. A similar arrangement is shown in FIG. 3D wherein both termini (or ends) of the wound dressing are devoid of a curved edge portion. In other words, at the both terminal ends, each of the: i) relevant transverse edge, ii) the first longitudinal edge and iii) the second longitudinal edge are devoid of a curved edge. The skilled person will appreciate that the wound dressing profiles depicted in FIGS. 3A-3D are for illustrative purposes only, and that any suitable number of curved edge portions along the first or second longitudinal edges may be employed in accordance with present invention.

In some embodiments, the curved edge portion of the first longitudinal edge has a corresponding profile to the curved edge portion of the second longitudinal edge, such that the first longitudinal edge tessellates with a second longitudinal edge of an identical wound dressing.

Figure 4:
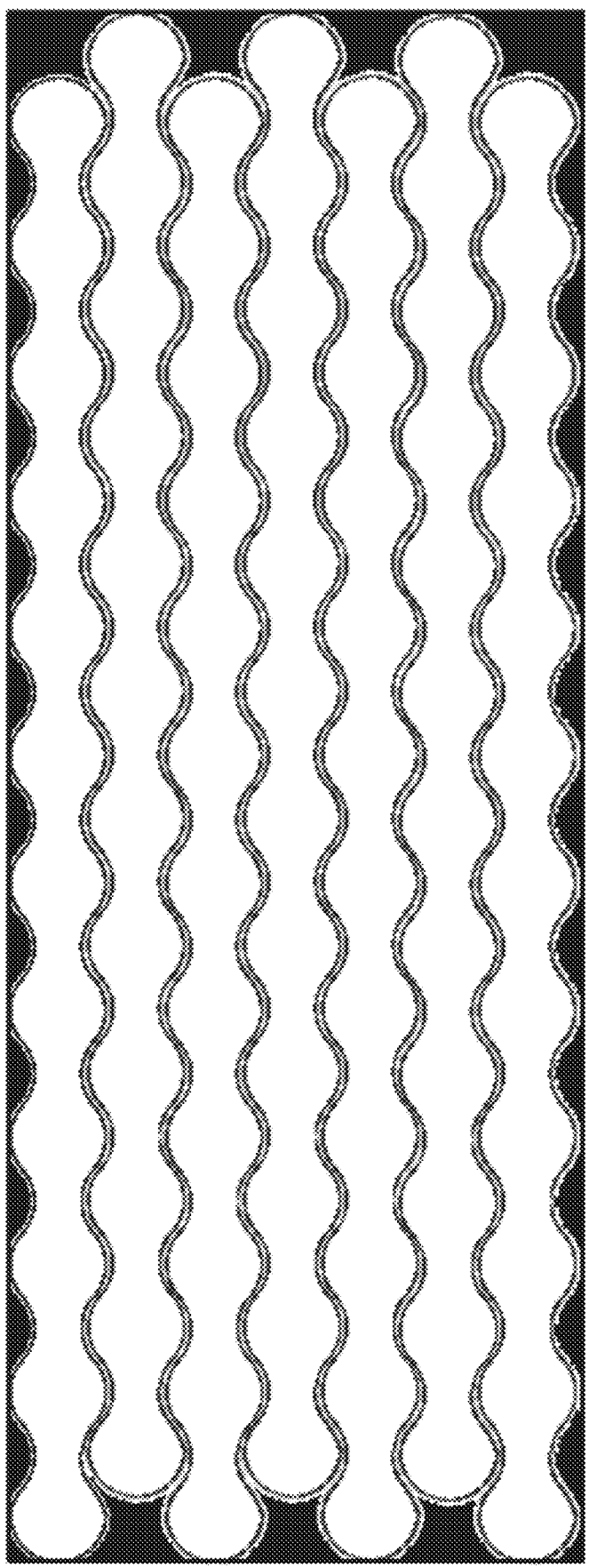
FIG. 4 depicts several tessellating wound dressings according to the present invention, shown within a sheet from which the wound dressings are cut during manufacture.

This arrangement is illustrated in FIG. 4, which depicts several adjacent wound dressings, wherein there is a negligible gap between each adjacent wound dressing.

Although FIG. 4 depicts the wound dressings tessellating by means of adjacent reciprocating curves, the skilled person will appreciate that any other tessellating shape may be used. As discussed in further detail below, tessellation of the wound dressings minimises the amount of waste off-cuts during the manufacturing process, the waste off-cuts being represented by the black shaded areas in FIG. 4.

In some embodiments, the elongate wound dressing is symmetrical in a plane that is perpendicular to the plane of the elongate wound dressing, and which bisects the wound dressing along central longitudinal axis A. Referring back to FIG. 2, it will be appreciated that the elongate wound dressing is symmetrical along central longitudinal axis A. In other words, in some embodiments, the profile of the curved edge portion of the first longitudinal edge may be a reflection of the profile of the curved edge portion of the second longitudinal edge in the longitudinal axis. However, in other embodiments, this need not be the case.

Figure 5A:
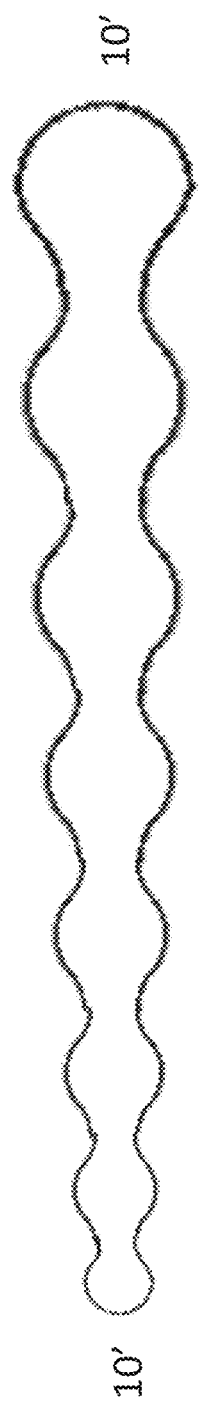
FIGS. 5A-5C depicts different illustrative embodiments of the present invention that are tapered along at least a portion of their length.
Figure 5B:
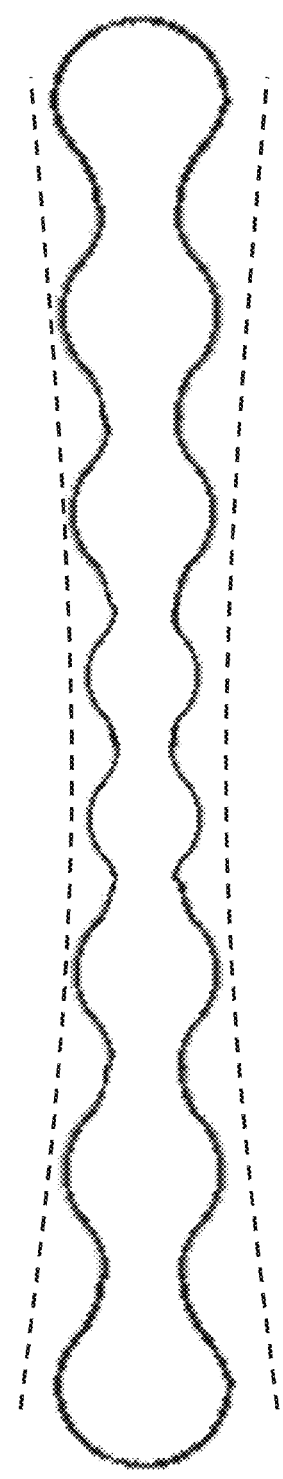
Figure 5C:
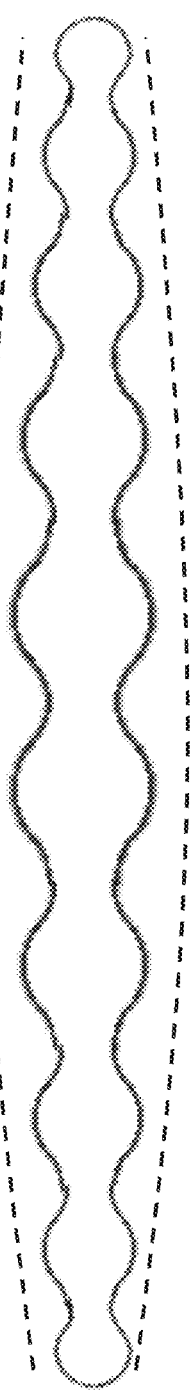

In some embodiments, the elongate wound dressing is tapered along its length in the plane of the wound dressing, and relative to the central longitudinal axis of the elongate wound dressing. The wound dressing may taper along its length from a widest portion at the first transverse edge 10 to a narrowest portion at the second transverse edge 10', as illustrated in FIG. 5A. In some embodiments, the wound dressing is tapered along its length from the first transverse edge 14 to a central portion (between the transverse edges), before broadening out again to the second transverse edge 14', as illustrated in FIG. 5B. In some embodiments, the wound dressing tapers from a central portion of the wound dressing (between the transverse edges of the wound dressing), and narrows towards the first 14 and second 14' transverse edges, as illustrated in FIG. 5C. The skilled person will appreciate that the wound dressing profiles depicted in FIGS. 5A-5C are for illustrative purposes only, and that any suitable tapering pattern may be employed in accordance with present invention.

In some embodiments, the curved edge portion may comprise a plurality of co-planar curved protrusions. The protrusions are co-planar such that when the wound dressing is folded, adjacent folded portions may overlie each other (e.g. substantially completely overlap each other) without substantial gaps or obstruction, that is to say, the folded portions may lie flush with one another. The co-planarity of the protrusions is discussed in further detail below.

Figure 6:
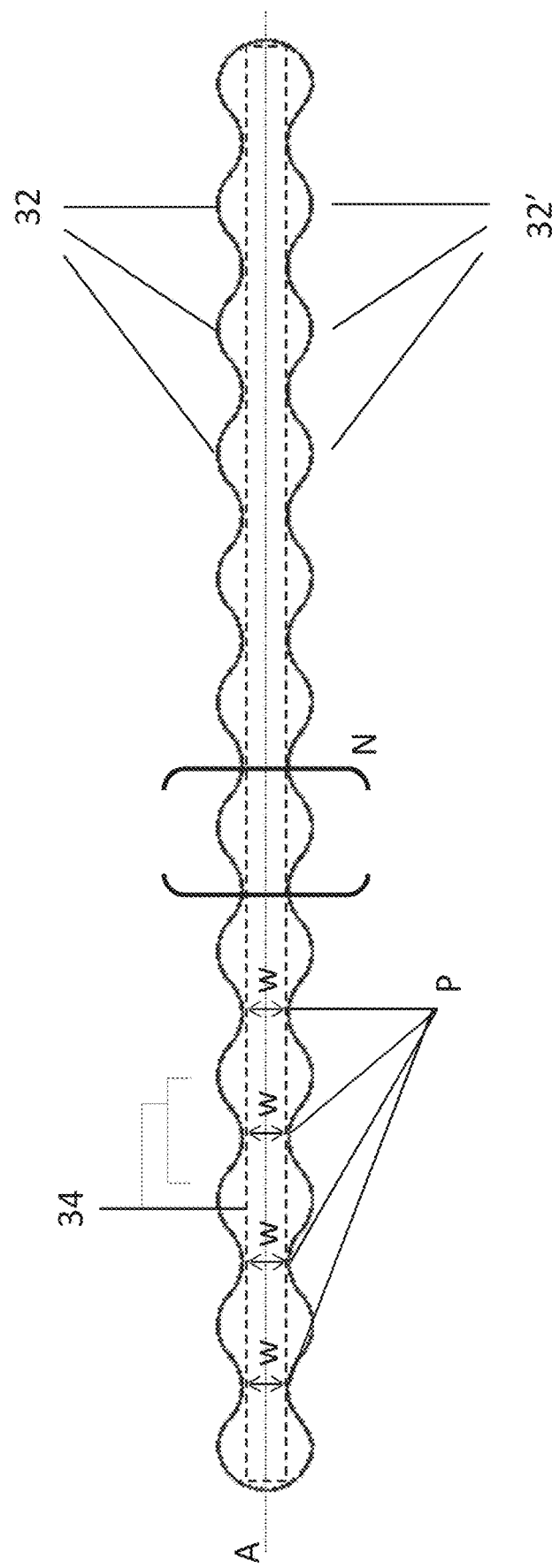
FIG. 6 depicts a plan view of an elongate wound dressing according to the present invention.

Referring to FIG. 6, the curved edge portion 2 of the first longitudinal edge 4 may comprise a plurality of curved protrusions 32, projecting outwardly in the plane of the dressing relative to the central longitudinal axis A of the wound dressing. Similarly, the curved edge portion 2' of the second longitudinal edge 4' may comprise a plurality of curved protrusions 32' projecting outwardly in the plane of the dressing relative to the central longitudinal axis A of the wound dressing. In some embodiments, each protrusion 32, 32' is convex in shape. In some embodiments, protrusions within a curved edge portion collectively form an undulating profile (i.e. wavy) along the curved edge portions 32, 32'. In some embodiments, the size and dimensions of the protrusions of a particular curved edge portion are the same. In some embodiments, the size and dimensions of the protrusions are variable between different curved edge portions (not illustrated). In some embodiments, the size and dimensions of the protrusions are variable within a curved edge portion (for example as illustrated in tapered examples FIGS. 5A-5B).

The dressing may be considered to comprise a notional rectangular central portion 34 having notional longitudinal edges from which the protrusions 32 may be considered to extend. Referring to FIG. 6, the rectangular central portion 34 may have a continuous width W (e.g. perpendicular to the axis A) along the length of the elongate wound dressing. The width W of the central rectangular portion 34 may be any suitable dimension. In some embodiments W is between 5 mm and 50 mm, optionally between 5 and 30 mm, further optionally between 5 and 20 mm. In some embodiments, W is around 10 mm.

The skilled person will understand that the notional rectangular central portion 34 may deviate from a rectangle, and may therefore be any other suitable quadrilateral. For example, in embodiments where the dressing is tapered the quadrilateral may be a trapezoid. In embodiments where the dressing is narrowest in the central portion (e.g. FIG. 5B) or at each end (e.g. FIG. 5C) the central portion may be hexagonal. In embodiments where the elongate wound dressing is tapered along a portion of its length, the notional width W of the notional central rectangular portion 32 may vary along the length of the ribbon wound dressing. In some embodiments the notional central portion may have notional longitudinal edges which are parallel to the longitudinal axis of the dressing. In embodiments in which the elongate dressing does not extend in a generally straight line, the longitudinal axis will also not be a straight line.

Referring to FIG. 6, portions P of the elongate wound dressing according to the present invention may have a width which corresponds to the width W of the central portion 6. These portions are typically devoid of protrusions 32, 32', or may be located between protrusions 32, 32'.

Figure 7:
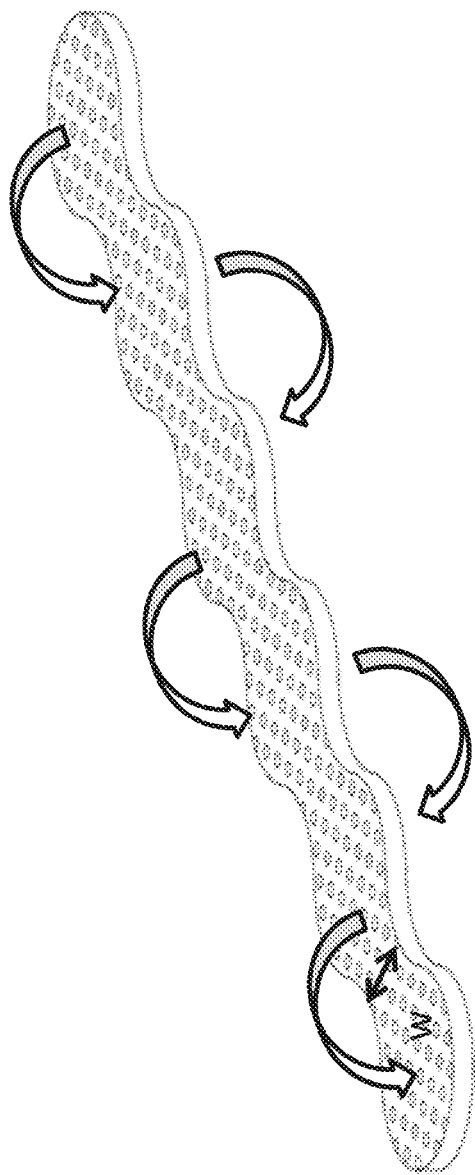
FIG. 7 depicts an illustrative perspective view of an elongate wound dressing according to the present invention, the arrows indicating the direction in which the wound dressing can be folded.
Figure 8:
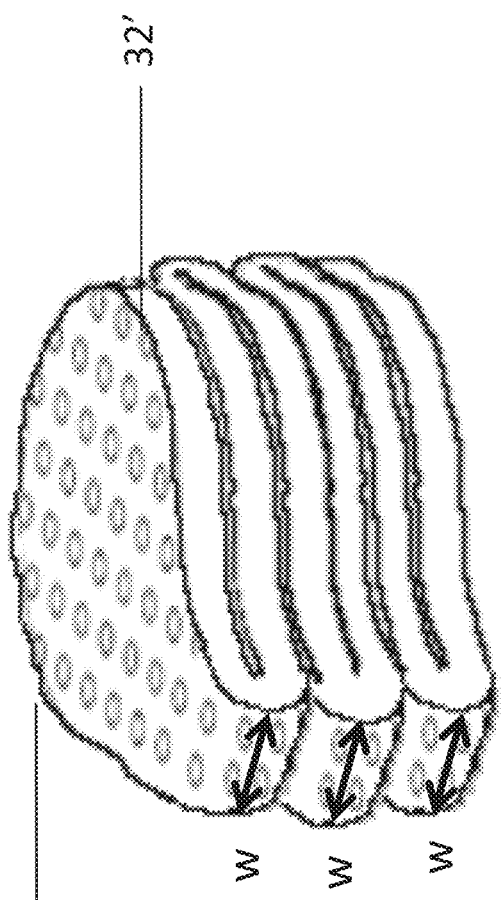
FIG. 8 depicts the elongate wound dressing of FIG. 7 that has been folded.

In some embodiments, the elongate wound dressing is folded in use along said portions of the elongate wound dressing having width W, as illustrated in FIG. 7. As can be seen in FIG. 8, once the wound dressing has been folded along portions of the wound dressing having width W, each protrusion 32, 32' may substantially overlap with an adjacent protrusion. When inserting the dressing into a wound, an extremity of the elongate wound dressing e.g. the first 10 or second 10' transverse edges, is placed into the wound and positioned towards the base thereof. The wound dressing is then folded in an alternating fashion as indicated by the arrows shown in FIG. 7, to provide a packed folded structure as shown in FIG. 8 within the wound. The curved edges of the curved edge portions when packed as illustrated in FIG. 8 mean that sharp edges are not in contact with the inner walls of the wound cavity. Furthermore, the curved edges better distribute the pressure exerted by the wound dressing over a larger surface area compared to the corners and sharp edges created when using conventional ribbon wound dressings.

Figure 9:
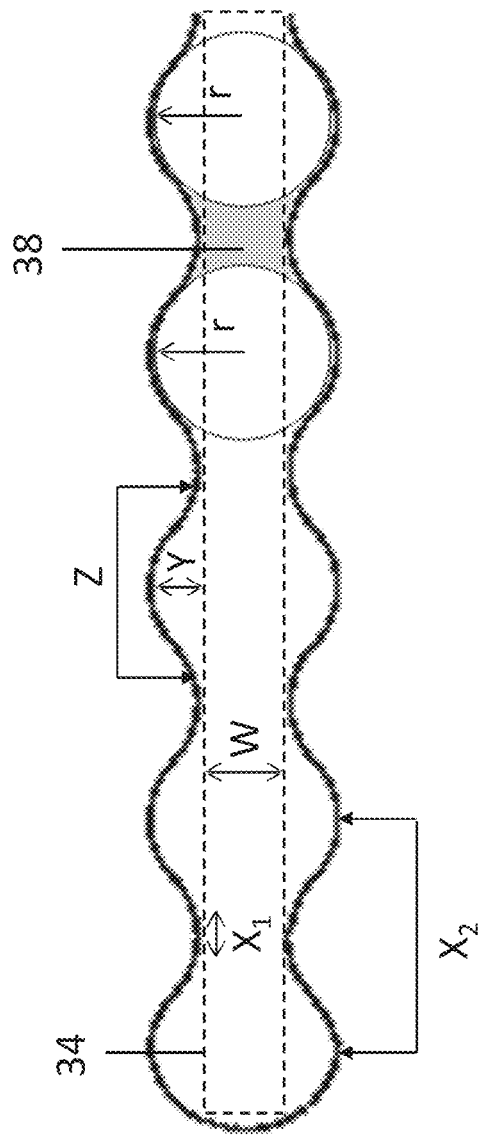
FIG. 9 depicts a magnified section of the elongate wound dressing depicted in FIG. 6.

In some embodiments, the protrusions 32 are axially separated by a distance $X_1$ with respect to the central longitudinal axis of the wound dressing. Referring to FIG. 9, in some embodiments the axial separation $X_1$ between adjacent protrusions may be uniform along the length of the curved edge portion. In some embodiments, the axial separation $X_1$ between adjacent protrusions may be different along the length of the curved edge portion. The axial separation between protrusions accommodates folding of the wound dressing such that a protrusion 32, 32' can substantially overlay an adjacent protrusion 32, 32' when folded. As such, the material which provides the axial separation acts as a bridge between folded portions of the elongate wound dressing. $X_1$ may be between 0.01 W and 2 W, optionally between 0.05 W and 1 W, and further optionally between 0.1 and 0.2 W.

The axial distance between the maxima of two curved protrusions may be defined by distance $X_2$. In some embodiments, the maxima between two curved protrusions may be between 0.5 W and 10 W, optionally between 1 W and 5 W, and further optionally around 2 W.

Referring to FIG. 9, the protrusions 32, 32' extend from the central rectangular portion 34 by a maximum distance Y. Y may be between 0.1 W and 2 W, optionally around 1 W. As such a protrusion 32 disposed on the first longitudinal edge 4 may increase the width of the dressing from W to between 1.1 W and 2 W.

The protrusions 32, 32' have a width with respect to the longitudinal axis of the elongate wound dressing of distance Z. Z may be between 0.1 and 2 times W, optionally around 1 W.

Figure 10:
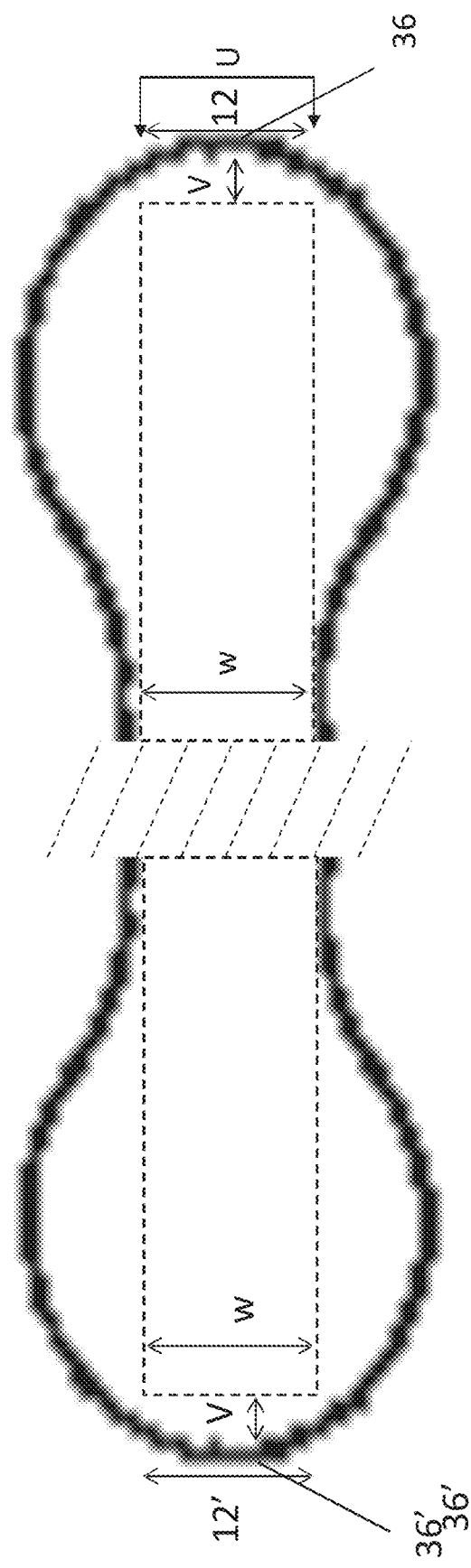
FIG. 10 depicts a magnified section of the elongate wound dressing depicted in FIG. 6.

In some embodiments, the first 10 and second 10' transverse edges may comprise at least one curved edge portion 12, 12'. The curved edge portions 12, 12' of the transverse edges may comprise one or more protrusions 36, 36'. Referring to FIG. 10, in some embodiments, the curved edge portion 12 of the first transverse edge 10 may comprise a single protrusion 36 extending from a notional transverse edge of the central rectangular portion 34 by distance V. In some embodiments, the curved edge portion 12' of the second transverse edge 10' may comprise a single protrusion 36' extending from a notional transverse edge of the central rectangular portion 34 by distance V. In some embodiments, the curved edge portions 12, 12' comprise a plurality of protrusions. V may be between 0.05 W and 1 W. As such, a single protrusion increases the length of the dressing L from L to between L+0.05 W, and L+W.

In some embodiments, the transverse width U of a single transverse protrusion 36 may be equal to W. The skilled person will appreciate that in embodiments where the curved edge portion 12 comprises a plurality of protrusions, the width of each protrusion will be a suitable fraction of W.

In some embodiments, each protrusion 32 has a corresponding protrusion 32' on the opposite longitudinal edge, such that the protrusions 32, 32' are aligned by an axis that is in the plane of the wound dressing and that is perpendicular to the central longitudinal axis. Referring back to FIG. 6, each protrusion 32 on the first longitudinal edge 4 is arranged directly opposite corresponding protrusions 32' on the second longitudinal edge 4'. In some embodiments, each protrusion 32 on the first longitudinal edge 4 may be of the same dimensions as the corresponding protrusion 32' on the second longitudinal edge 4', such that each protrusion is disposed opposite an identical protrusion. In embodiments where each protrusion 32 has an identical protrusion 32' on the opposite longitudinal edge, the elongate wound dressing may be symmetrical about the central longitudinal axis. In embodiments where the protrusion 32 has a corresponding protrusion 8' disposed on the second longitudinal edge 4', the width of the dressing may be increased from W to a maximum width of about 1.2 to 3 times W.

In some embodiments, each transverse protrusion 36 has a corresponding protrusion 36' on the opposite transverse edge, such that the protrusions 36, 36' are aligned in the central longitudinal axis A and in the plane of the wound dressing.

In some embodiments, and with reference to FIG. 6, where the elongate wound dressing comprises protrusions 32 on a first longitudinal edge 4 and protrusions 32' on a second longitudinal edge 4', the elongate wound dressing may include (or visually represent) a plurality of repeating units (N) along at least a portion of the wound dressing's longitudinal length. Any number of repeating units (N) may be included in the elongate wound dressing. Where the elongate wound dressings are provided ready for use, (N) may be between 10 and 30. Where the elongate wound dressings are provided as a roll which may then be cut to size of use, (N) may be any suitable number, which may be between 100 and 20,000.

In some embodiments, the repeating units (N) may be considered to represent a plurality of bridged and coalescing circles, as illustrated in FIG. 9. Circles having radius r are linked by an axial separation portion 38 (shaded region in FIG. 9). The radius of circle r may be between 0.5 and 2 W, optionally around 1 W.

In some embodiments wherein a longitudinal edge comprises more than one curved edge portion, each curved edge portion may have an axial separation. Referring back to FIGS. 3A and 3B, regions 18, 26 and 28 that are devoid of a curved edge portion may be considered as the axial separation between curved edge portions. The axial separation between curved edge portions may be between 0.1 W and 10 W, optionally between 0.5 W and 5 W, and further optionally around 1 W.

In some embodiments, the elongate wound dressings according to the present invention have a laminate structure. This laminated structure may be applied to any of the shapes of elongate wound dressing discussed above, or any other shape of elongate wound dressing, as appropriate.

Figure 11:
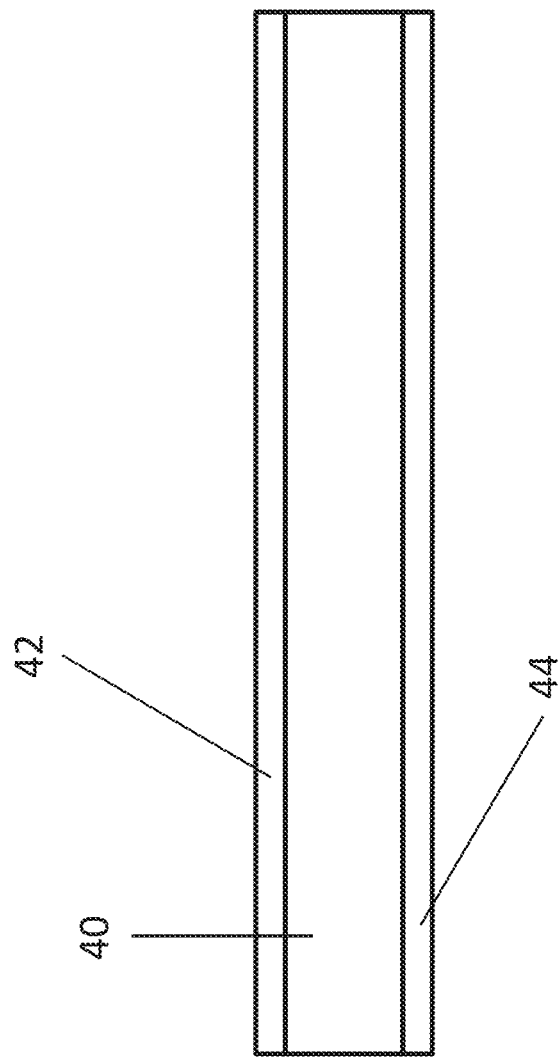
FIG. 11 depicts an illustrative cross-section of an elongate wound dressing according to the present invention.

As depicted in FIG. 11, elongate wound dressings according to the present invention may comprise an absorbent layer 40, preferably a hydrophilic absorbent layer. In embodiments, the absorbent layer is sandwiched between a first non-adherent layer 42 and a second non-adherent layer 44. The non-adherent layers 42, 44 aid in ensuring continued integrity of the absorbent layer 40 after use, and in preventing adhesion of the wound dressing to the wound walls. The non-adherent layers 42, 44 may be breathable polymeric films or meshes such as, but not limited to, polyurethane, polyethylene and polypropylene. In embodiments, at least one non-adherent layer 42, 44 may be perforated, as shown by the small circular shapes on the upper surface of the wound dressings in FIGS. 7 and 8.

In some embodiments the absorbent layer 40 comprises absorbent foam, which advantageously provides an effective absorbent core for exudates, but which advantageously retains its structural integrity following absorption of exudates. Furthermore, the absorbent foam may be non-adherent. In addition the absorbent foam does not expand significantly on absorption of exudate, thereby reducing the pressure exerted on the wound walls by the wound dressing and minimising wound healing disruption during use. Suitable absorbent foams include, but are not limited to, polyurethane, polyethylene and polypropylene foams. The absorbent foam may be able to absorb between 0.1 g/g and 100 g/g/of fluid, optionally between 0.5 g/g and 50 g/g of fluid, and further optionally between 1 g/g and 25 g/g of fluid.

In some embodiments, the absorbent layer 40 may comprise non-woven hydrophilic fibres comprising alginate, sodium carboxymethyl cellulose, ethyl sulphonate cellulose fibres, polyvinyl alcohol fibres, chitosan gelling fibres, or combinations thereof. In such embodiments, the laminated structure advantageously ensures the non-woven hydrophilic fibre absorbent layer (which may be prone to disintegration following absorption of wound exudates) retains its structural integrity by virtue of being provided between non-adherent layers 40, 42. In other words, the non-adherent layers act as a structural support for the non-woven fibre absorbent layer.

The non-adherent layers 40, 42 and absorbent layer 40 may be laminated together by means of a medically acceptable adhesive, such as, but not limited to acrylics, silicones, low and high density polyethylenes (LDPE, HDPE), ethylene vinyl acetates (EVA), thermoplastic polyurethanes (TPU) and polyamide adhesives. The resulting laminate structure may then be cut using a rolling die, or any other suitable apparatus. The tessellating profile of the wound dressings in embodiments of the present invention minimises waste material being created when the wound dressing are cut by the rolling die in the manufacturing process. Referring back to FIG. 4, waste material is minimised where the wound dressings to be cut tessellate, as each cut forms an edge of two separate wound dressings. Only regions shaded in black are disposed of as waste. As such, wound dressings according to embodiments of the present invention reduce manufacturing costs, whilst simultaneously mitigating the effects of sharp edges on wounds.

In some embodiments, the overall length L of the wound dressing is between 100 mm and 1000 mm, optionally between 200 mm and 500 mm and further optionally between 300 mm and 400 mm. Of course, the wound dressing may be provided in such pre-determined lengths, or alternatively as a roll which may be cut to a suitable length.

The laminate structure of the wound dressings further provides improved tensile properties compared to existing wound dressings. The laminate structure allows the wound dressing to be handled in both dry and wet state without comprising structural integrity. The laminate structure also aids the conformability of the elongate wound dressing during packing.

The invention claimed is:

1. A ribbon wound dressing for packing a wound, the ribbon wound dressing being substantially planar and having:
   a first longitudinal edge comprising at least one curved edge portion that is curved in the plane of the ribbon wound dressing, wherein:
      the at least one curved edge portion comprises a plurality of co-planar curved protrusions projecting outwardly relative to a central longitudinal axis of the ribbon wound dressing and in the plane of the ribbon wound dressing,
      the at least one curved edge portion comprises a plurality of co-planar curved recesses,
      each of the plurality of co-planar curved protrusions are concave in a first direction,
      each of the plurality of co-planar curved recesses are concave in a second direction,
      the first direction is opposite to the second direction, and
      the plurality of co-planar curved protrusions and the plurality of co-planar curved recesses form a continuous undulating profile devoid of any sharp corners along the at least one curved edge portion; and
      portions located between adjacent protrusions having a width that corresponds to the width of a central portion of the ribbon wound dressing and each of the portions being suitable as a single folding juncture between adjacent protrusions, wherein in use, the ribbon wound dressing is folded along said portions in an alternating fashion to provide a packed folded structure,
   wherein the ribbon wound dressing is non-adherent.

2. The ribbon wound dressing according to claim 1 comprising an absorbent layer, a first non-adherent layer, and a second non-adherent layer, wherein the absorbent layer is disposed between the first non-adherent layer and the second non-adherent layer.

3. The ribbon wound dressing according to claim 2 wherein the first non-adherent layer and/or the second non-adherent layer is perforated.

4. The ribbon wound dressing according to claim 2 wherein the absorbent layer comprises a foam.

5. The ribbon wound dressing according to claim 4 wherein the absorbent layer comprises polyurethane foam.

6. The ribbon wound dressing according to claim 2 wherein the absorbent layer does not substantially expand when the absorbent layer is saturated with wound exudates.

7. The ribbon wound dressing according to claim 1 having a second longitudinal edge comprising at least one curved edge portion that is curved in said plane of the ribbon wound dressing.

8. The ribbon wound dressing according to claim 7 wherein the at least one curved edge portion of the first longitudinal edge has a corresponding profile to the at least one curved edge portion of the second longitudinal edge, such that the first longitudinal edge of the ribbon wound dressing tessellates with a second longitudinal edge of an identical ribbon wound dressing.

9. The ribbon wound dressing according to claim 7 wherein the ribbon wound dressing is symmetrical in a plane that is perpendicular to the plane of the ribbon wound dressing, and which bisects the ribbon wound dressing along a central longitudinal axis.

10. The ribbon wound dressing according to claim 1 having a rectangular central portion of width W, wherein each of the plurality of co-planar curved protrusions extends outwardly to increase the maximum width of the ribbon wound dressing by between 1.1 times W and 2 times W.

11. The ribbon wound dressing according to claim 10 having a rectangular central portion of width W, wherein each of the plurality of co-planar curved protrusions extends outwardly to increase the maximum width of the ribbon wound dressing by 1.5 times W.

12. The ribbon wound dressing according to claim 1 wherein the ribbon wound dressing is tapered along at least a portion of its length in the plane of the ribbon wound dressing relative to a central longitudinal axis of the ribbon wound dressing.

13. The ribbon wound dressing according to claim 1 having a central rectangular portion of width W, wherein the plurality of co-planar curved protrusions project outwardly from a notional longitudinal edge of the central rectangular portion, wherein the notional longitudinal edge of the central rectangular portion is parallel to the central longitudinal axis of the ribbon wound dressing.

14. The ribbon wound dressing according to claim 1 having a rectangular central portion of width W wherein the ribbon wound dressing is foldable along portions of the ribbon wound dressing of width W.

15. The ribbon wound dressing according to claim 1 wherein adjacent protrusions are axially separated with respect to the central longitudinal axis of the ribbon wound dressing.

\* \* \* \* \*